United States Patent
Haugaard et al.

(10) Patent No.: US 9,170,330 B2
(45) Date of Patent: Oct. 27, 2015

(54) VELOCITY ESTIMATION FOR VECTOR FLOW IMAGING (VFI) IN ULTRASOUND

(75) Inventors: Per Haugaard, Skovlunde (DK); Gert Seerup, Hilleroed (DK)

(73) Assignee: Analogic Corporation, Peabody, MA (US)

(*) Notice: Subject to any disclaimer, the term of this patent is extended or adjusted under 35 U.S.C. 154(b) by 230 days.

(21) Appl. No.: 13/613,869

(22) Filed: Sep. 13, 2012

(65) Prior Publication Data
US 2014/0073923 A1    Mar. 13, 2014

(51) Int. Cl.
*A61B 8/06* (2006.01)
*G01S 15/89* (2006.01)

(52) U.S. Cl.
CPC ............... *G01S 15/8984* (2013.01); *A61B 8/06* (2013.01); *G01S 15/8915* (2013.01)

(58) Field of Classification Search
CPC ............ A61B 8/08; A61B 8/06; A61B 8/488; G01S 15/582
See application file for complete search history.

(56) References Cited

U.S. PATENT DOCUMENTS

| | | | |
|---|---|---|---|
| 5,855,557 A | 1/1999 | Lazenby | |
| 6,148,224 A | 11/2000 | Jensen | |
| 6,618,493 B1* | 9/2003 | Torp et al. | 382/131 |
| 6,859,659 B1 | 2/2005 | Jensen | |
| 2011/0218435 A1* | 9/2011 | Srinivasan et al. | 600/441 |

* cited by examiner

*Primary Examiner* — Mark Remaly
(74) *Attorney, Agent, or Firm* — Anthony M. Del Zoppo, III; Driggs, Hogg, Daugherty & Del Zoppo Co. LPA

(57) ABSTRACT

An ultrasound imaging system includes a transducer array, with an array of transducer elements that transmits an ultrasound signal and receives a set of echoes generated in response to the ultrasound signal traversing a flowing structure. The ultrasound imaging system further includes a beamformer that beamforms the set of echoes, generating a beamformed signal. The ultrasound imaging system further includes a pre-processor that performs basebanding, averaging and decimation of the beamformed signal and determines an autocorrelation of the basebanded, averaged and decimated beamformed signal. The ultrasound imaging system further includes a velocity processor that generates an axial velocity component signal and a lateral velocity component signal based on the autocorrelation. The axial and lateral velocity components indicate a direction and a speed of the flowing structure in the field of view.

12 Claims, 3 Drawing Sheets

VELOCITY ESTIMATION FOR VECTOR FLOW IMAGING (VFI) IN ULTRASOUND

TECHNICAL FIELD

The following generally relates to ultrasound imaging and more particularly to velocity estimation for a VFI ultrasound imaging.

BACKGROUND

Ultrasound imaging provides a real-time image with information about the interior of an object or subject such as an organ, a blood vessel, etc., and/or the flow inside a blood vessel.

Color flow mapping (CFM) is an approach used to estimate and visualize the flow inside blood vessels. CFM can be realized efficiently and made feasible using a low-cost velocity estimator. Unfortunately, CFM can only show the relative blood flow information of whether the flow is towards or away from the transducer. Hence, it does not show the absolute flow direction nor absolute velocities, and it is operator dependent.

Vector flow imaging (VFI) is another approach used to estimate and visualize the flow inside a blood vessel. VFI ultrasound imaging can simultaneously show both the absolute flow direction and the absolute velocity. However, VFI velocity estimators have had significantly higher "computational requirements" and hence more computational resources to realize images with similar resolution and framerate as CFM.

As used herein, the term "computational requirement" includes the number of operations in computing a given function. As used herein, the term "operation" includes at least a real-valued multiply-accumulate operation, a real-valued multiply-add, a real-valued multiply or a real-valued addition/subtraction operation.

This need for more computational resources for implementing VFI may add cost to a new ultrasound imaging system, relative to a new ultrasound imaging system without VFI capabilities, and/or prohibit VFI from being implemented on an existing ultrasound imaging system.

SUMMARY

Aspects of the application address the above matters, and others.

In one aspect, an ultrasound imaging system includes a transducer array, with an array of transducer elements that transmits an ultrasound signal and receives a set of echoes generated in response to the ultrasound signal traversing a flowing structure. The ultrasound imaging system further includes a beamformer that beamforms the set of echoes, generating a beamformed signal. The ultrasound imaging system further includes a pre-processor that performs basebanding, averaging and decimation of the beamformed signal and determines an autocorrelation of the basebanded, averaged and decimated beamformed signal. The ultrasound imaging system further includes a velocity processor that generates an axial velocity component signal and a lateral velocity component signal based on the autocorrelation. The axial and lateral velocity components indicate a direction and a speed of the flowing structure in the field of view.

In another aspect, a method includes receiving a set of echoes generated in response to an ultrasound signal traversing a flowing structure in a field of view. The method further includes beamforming the set of echoes, generating a beamformed signal. The method further includes basebanding, averaging and decimating the beamformed signal. The method further includes determining, via a processor, an autocorrelation of the basebanded, averaged and decimated beamformed signal. The method further includes generating an axial velocity component signal and a lateral velocity component signal based on the autocorrelation. The axial and lateral velocity components indicate a direction and a speed of the flowing structure in the field of view In another aspect, a pre-processor for a velocity processor of an ultrasound console configured for velocity flow imaging, the pre-processor includes a basebander that demodulates the input beamformed signals into an basebanded complex signal, an averager that averages a set of input beamformed signals, a decimator that decimates the averaged set of beamformed signals by a decimation factor in a range of two to eight, and an autocorrelator that determines an autocorrelation of the basebanded, averaged and decimated set of beamformed signals. The autocorrelation is used to generate an axial velocity component signal and a lateral velocity component signal.

Those skilled in the art will recognize still other aspects of the present application upon reading and understanding the attached description.

BRIEF DESCRIPTION OF THE DRAWINGS

The application is illustrated by way of example and not limited by the figures of the accompanying drawings, in which like references indicate similar elements and in which.

DETAILED DESCRIPTION

The following describes an approach to VFI ultrasound imaging in which the beamformed data is basebanded, averaged and decimated prior to autocorrelation. As described in detail below, in one instance, this allows for reducing the computational requirements of the VFI velocity processor for an ultrasound VFI imaging system (e.g., by up to 30×, such as 20×) with no visible loss of information, providing VFI at low-cost to new and/or existing ultrasound imaging systems.

Figure 1:
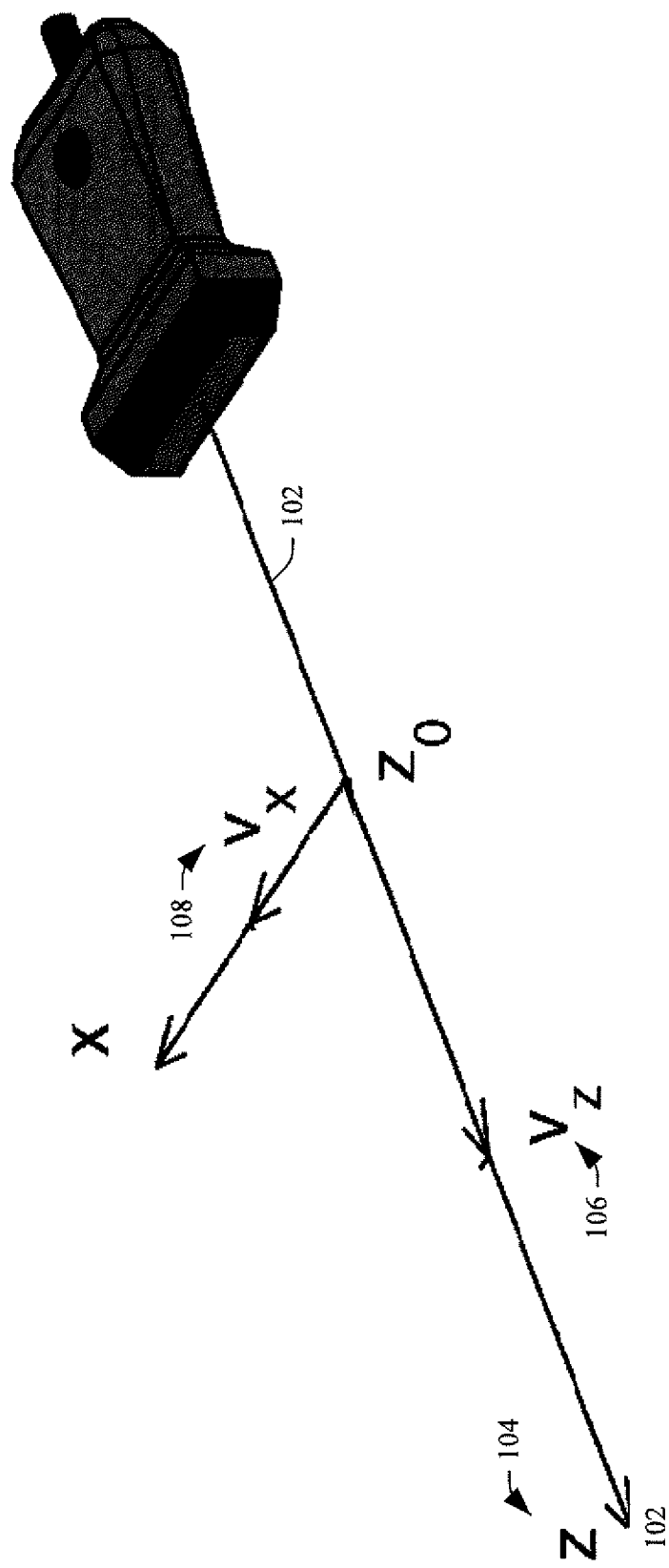
FIG. 1 illustrates the axial velocity (Vz) and lateral velocity (Vx) components of a transmitted ultrasound signal.

U.S. Pat. No. 6,859,659 B1 to Jensen, which is incorporated herein by reference in its entirety, describes an approach for estimating the axial velocity component (Vz) and the lateral velocity component (Vx). As shown in FIG. 1, Vz is the velocity along the axial direction, which is a direction of the propagating beam, and Vx is the velocity along a lateral direction, which is transverse to the axial direction.

As described in U.S. Pat. No. 6,859,659 B1, the lateral velocity component (Vx) can be determined as shown in EQUATION 1:

$$Vx(n) = \left(\frac{d_x}{2\pi 2 T_{prf}}\right) \qquad \text{EQUATION 1}$$

$$\arctan\left(\frac{\Im\{R1_1(n)\}\Re\{R2_1(n)\} + \Im\{R2_1(n)\}\Re\{R1_1(n)\}}{\Re\{R1_1(n)\}\Re\{R2_1(n)\} - \Im\{R2_1(n)\}\Im\{R1_1(n)\}}\right),$$

where n is the sample number, $d_x$ is the lateral modulation period, $T_{prf}$ is the time between pulse emissions, $\Im\{R1_1(n)\}$ is the imaginary part of the complex lag one autocorrelation value for $r_1(i,n)=r_{sq}(i,n)+jr_{sqh}(i,n)$, where sq represents the received and sampled in phase spatial quadrature filed, and $\Re\{R2_1(n)\}$ is the real part of the complex lag one autocorrelation value for $r_2(i,n)=r_{sq}(i,n)-jr_{sqh}(i,n))$, where sqh represents temporal quadrature spatial quadrature field signal (or the Hilbert transform of sq).

The axial velocity component (Vz) can be determined from the conventional autocorrelation estimator as shown in EQUATION 2:

$$Vz(n) = \left(\frac{c}{2\pi 2T_{prf}f_o}\right) \arctan\left(\frac{\Im\{R_1(n)\}}{\Re\{R_1(n)\}}\right), \quad \text{EQUATION 2}$$

where c is the speed of sound and $f_o$ is the center frequency and R(n) is the complex lag one autocorrelation of the input signal r(i, n).

The velocity estimator of U.S. Pat. No. 6,859,659 B1 produces estimates for acquired RF-samples independently of the actual number of pixels to display each scan-line in order to average the autocorrelation estimate over a length of an interrogating pulse, which may facilitate optimizing the signal-to-noise ratio. With a pulse length in terms of RF samples given by $N_p=(M/f_o)\cdot f_s$, where M is the number of periods and $f_s$ is the sampling frequency, the average autocorrelation estimates can be determined as shown in EQUATION 3:

$$\bar{R}_k(n_o) = \frac{1}{(N-k)N_P}\sum_{i=0}^{N-k}\sum_{n=-\frac{N_p}{2}}^{\frac{N_p}{2}-1} r^*(i, n+n_o)r(i+k, n+n_o), \quad \text{EQUATION 3}$$

where N is the number of shots per estimated sample, r(i,n) is the RF sample of the received signal shot i and sample n. r*(i,n) is the complex conjugate of r(i,n). The number of operations in the autocorrelation-average $O_{corravg}(N,N_p)=N*N_p$, leaving out k, which $\approx 1$, for simplicity.

For the estimation of Vx, two autocorrelation-average computations are calculated for each scan-line, one for each of the two input signals $r_1(i,n)$ and $r_2(i,n)$ from the two beams acquired for the estimation of Vx. The number of operations in the Vx autocorrelation-average computation for a frame of L lines and M samples per line becomes $O_{corravg,x}(L,M,N,N_p)=2*L*M*N*N_p$.

For the estimation of Vz, a single autocorrelation-average computation is calculated, and the number of operations in the Vz autocorrelation-average computation for a frame of L lines and M samples per line becomes $O_{corravg,z}(L,M,N,N_p)=L*M*N*N_p$. The total number of operations is $O_{corravg,x}(L,M,N,N_p)+O_{corravg,z}(L,M,N,N_p)=O_{corravg}(L,M,N,N_p)=3*L*M*N*N_p$.

Averaging the autocorrelation estimate as such can be computationally expensive and may require additional computation resources, which adds cost to a new ultrasound system and/or possibly prohibits VFI from being implemented with an existing ultrasound system. An alternative approach is to perform basebanding, averaging and decimation of the received signal prior to autocorrelation. The basebanding circuitry can be reused from the B-mode signal processing chain avoiding added cost and/or computational requirements.

Figure 2:
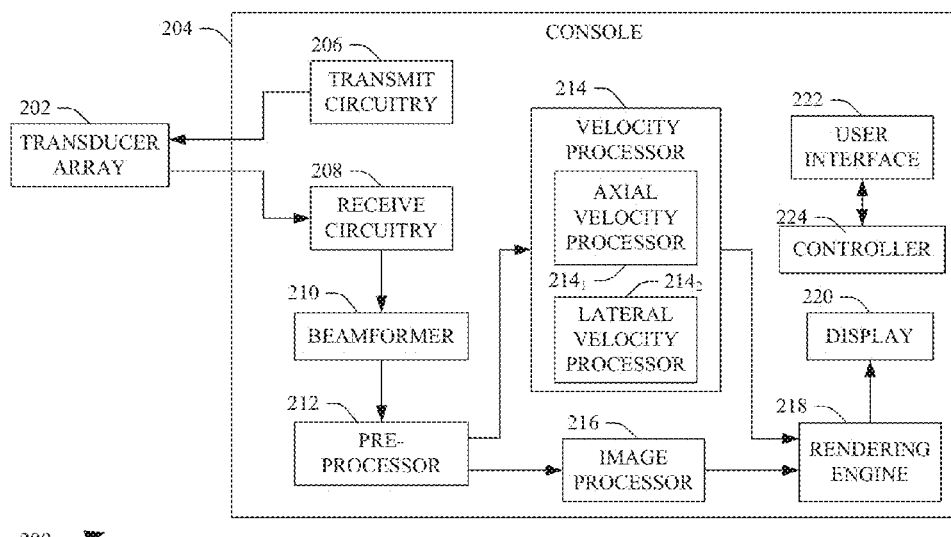
FIG. 2 schematically illustrates an example ultrasound imaging system with a pre-processor that processes beamformed data to be used to estimate the axial velocity (Vz) and lateral velocity (Vx) components.

Turning now to FIG. 2, an example ultrasound imaging system 200 is schematically illustrated.

The system 200 includes a transducer array 202 that interfaces with a console 204 via a suitable wire and/or wireless interface. Generally, the transducer array 202 converts an electrical signal to an ultrasound pressured field and vice versa. More specifically, the transducer array 202 includes an array of transducer elements that are configured to transmit ultrasound signals and receive echo signals. Examples of suitable arrays include 128, 192, and/or other elements arrays, including rectangular arrays. The array can be linear, curved, and/or otherwise shaped, fully populated, sparse and/or a combination thereof, etc.

Transmit circuitry 206 generates a set of pulses (or a pulsed signal) that are conveyed to the transducer array 202. The set of pulses actuates a set of the transducer elements of the transducer array 202, causing the elements thereof to transmit ultrasound signals into an examination or scan field of view. In the illustrated embodiment, transmit circuitry 206 generates a set of pulses which produce a transmit signal suitable at least for VFI imaging.

Receive circuitry 208 receives a set of echoes (or echo signals) generated in response to the transmitted ultrasound signals, for example, in response to the ultrasounds field traversing an object such as blood flowing in a portion of a vessel in a region of interest in the scan field of view and/or other structure. The echoes, generally, are a result of the interaction between the emitted ultrasound signals and the object (e.g., flowing blood cells, organ cells, etc.) in the scan field of view.

A beamformer 210 processes the echoes, for example, by applying time delays to echoes, weighting echoes, summing delayed and weighted echoes, and/or otherwise beamforming received echoes, creating a beam of RF data. In one instance, for VFI, the beamformer 210 produces three beams for each scan line, one beam for an estimate of the Vz component and two beams for an estimate of the Vx component. The illustrated beamformer 210 produces two or more scan lines, in parallel, for each acquisition event. In other embodiment, the beamformer 210 can generate more or less beams and/or scan-lines for the Vz and/or Vx components, for example 4 beams per 2 scan-lines.

A pre-processor 212 pre-processes the beamformed scan-lines. As discussed in greater detail below, such pre-processing includes basebanding, averaging and decimating the received scan-lines and then determining an autocorrelation of the averaged-decimated scan-lines. In one instance, this allows for reducing the computational requirements of the Vz and Vx estimates, relative to a configuration which does not average and decimate prior to autocorrelating, such as the autocorrelate-average configuration discussed above in connection with U.S. Pat. No. 6,859,659 B1. The pre-processor 212 can be configured to perform other functions such as echo-cancellation, wall-filtering, and/or other functions associated with VFI imaging and/or other imaging.

A velocity processor 214 processes the pre-processed data. For example, in one instance the velocity processor 214 processes the data and generates velocity components Vz and Vx based on EQUATIONS 1 and 2 and/or otherwise. The axial and lateral velocity components indicate a direction and a speed of flowing structure in the field of view. The illustrated velocity processor 214 includes an axial velocity processor $214_1$ that processes generates the Vz velocity component and a transvers velocity processor $214_2$ that processes generates the Vx velocity component. In a variation, the same processor generates both Vz and Vx. In another variation, two or more processors generate at least one of Vz or Vx.

An image processor 216 also processes the pre-processed data. For B-mode imaging, this includes envelope detection and log-compression. The image processor 216 may also process scan-lines to lower speckle and/or improve specular reflector delineation, and/or perform other processing such as FIR and/or IIR filtering, etc.

A rendering engine 218 visually presents one or more images and/or velocity information via a display monitor 220, which can be part of the console 204 (as shown) or separate from the console 204. Such presentation can be in an interactive graphical user interface (GUI), which allows the user to selectively rotate, scale, and/or manipulate the displayed data. Such interaction can be through a pointer like a mouse, a keyboard, etc., and/or other known and/or approach for interacting with a GUI. In one instance, indicia representing the velocity components are displayed superimposed over another image such as a B-mode image and/or other image. Such indicia may include color, gray scale, arrows, and/or other indicia.

A user interface (UI) 222 include one or more input devices (e.g., a button, a knob, a slider, a touch pad, etc.) and/or one or more output devices (e.g., a display screen, lights, a speaker, etc.), which allow for interaction between a user and the ultrasound imaging system 102. A controller 222 controls one or more of the components of the console 204. Such control can be based on available modes of operation (e.g., velocity flow, B-mode, etc.), e.g., as selected via the UI 222 by a user.

It is to be appreciated that the beamformer 210, the pre-processing component 212, and/or the velocity processor 216 can be implemented via one or more processors executing one or more computer readable instructions encoded or embedded on computer readable storage medium such as physical memory or other non-transitory medium. Additionally or alternatively, at least one of the instructions can be carried by a carrier wave, a signal, or other transitory medium.

Figure 3:
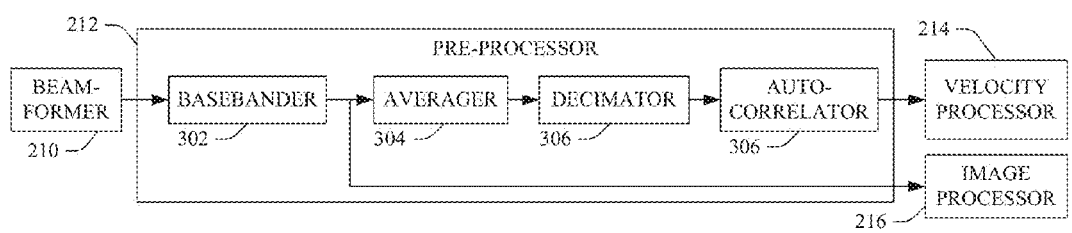
FIG. 3 schematically illustrates an example of the pre-processor.

FIG. 3 shows an example of the pre-processing component 212, which includes a bandbander (or basebanding circuitry) 302, an averager 304, a decimator 306, and an autocorrelator 308. In a variation, one or more of the bandbander 302, the averager 304, the decimator 306, and the autocorrelator 308 is not part of the pre-processing component 212, but instead is part of the velocity processor 214 and/or other component.

In this example, the basebander 302 demodulates the input beamformed signals into a basebanded complex signal, and the averager 304 averages the received signal based on EQUATION 4:

$$s(i, m) = \frac{1}{N_P} \sum_{u=-N_P/4}^{N_P/4-1} r(i, 2u + n_o), n_o = mQ,$$ EQUATION 4 the combination of the basebander 302 and the decimator 306 decimates the averaged signal by Q, and the autocorrelator 308 determines the autocorrelation of the averaged-decimated signal based on the lag k autocorrelation estimate shown in EQUATION 5:

$$\overline{R}_k(m) = \frac{1}{(N-k)} \sum_{i=0}^{N-k} s^*(i, m)s(i+k, m),$$ EQUATION 5 where $Q \geq 2$ is the RF-samples-to-pixels decimation factor, r(i, n) is the base-banded (I,Q)-sample for acquisition event i and RF-sample n, r(i, 2n) is the base-banded and decimated-by-2 (I,Q)-sample for acquisition event i and RF-sample 2n.

The number of operations of the Vx average-and-correlate is $O_{avecorr,x}(L,M,N,N_p,Q)=L*M*N*(N_p+4)/Q$, leaving out k, which ≈1, for simplicity. The number of operations of the average-and-correlate vector-velocity estimation for a frame of L lines and M samples per line is $O_{avecorr,z}(L,M,N,N_p,Q)+O_{avecorr,x}(L,M,N,N_p,Q)=O_{avecorr}(L,M,N,N_p,Q)=3*L*M*N*(N_p+4)/Q$.

The average s(i, m) and decimate by Q operations of the received signal can be performed in hardware (e.g., addition-operations only) by a firmware only upgrade without adding cost to the system. This reduces the number of operations of the Vx average-and-correlate vector-velocity estimation $O_{avecorr,x}(L,M,N,Q)=2*L*M*N*4/Q$. (For a base ultrasound CFM system, this reduces the number of operations for the base case CFM to $O_{corrbase}(L,M,N,Q)=L*M*N*4/Q$.)

The number of operations of the average-and-correlate vector-velocity estimation for a frame of L lines and M samples each line then is $O_{avecorr,z}(L,M,N,Q)+O_{avecorr,z}(L,M,N,Q)=O_{avecorr}(L,M,N,Q)=3*L*M*N*4/Q$, and the computational requirements of the autocorrelation for the combination of the 4-beams-2-lines beam-former and the average-and-correlate vector-velocity estimation is $O_{avecorr,z}(L,M,N,Q)+O_{avecorr,x}(L/2M,N,N_p,Q)=2*L*M*N*4/Q$.

Various approaches can be used to select a Q. For example of speed of sound C=1540 m/s, center receive frequency of $F_0$=5 MHz, acquisition depth D=10 cm, and sample frequency of $F_s=4*F_0$, the scan-line length is M=2*D/$C*F_s$=2597 RF-samples, and M/2=1298 complex (I,Q)-samples, even when only 512 pixels are to be displayed each scan-line. This scan-line represents an oversampled signal as the input signal bandwidth is only approximately ¼ when a transmit pulse of $4*F_0$ periods is used.

With a $F_s=3*F_0$, the scan-line length is M=1948, and M/2=974. Thus, the received signal can be decimated by a factor at least up to four (4) with little or no loss of information. At least a decimation with a factor of two (2) can be applied with no loss of information while leaving bandwidth for a non-ideal average/decimation filter response, resulting in a scan-line length of M/2=974 samples and M/4=487 samples. In another example, the factor has a value in a range from two (2) to eight (8).

The following provides an example of a comparison between the number of computational operations of the average and correlate approach described herein and other approaches.

The computational requirements of the correlate and average velocity estimator of U.S. Pat. No. 6,859,659 B1 relative to the average and correlate computation of a base CFM system for Q=4 and $N_p$=16 is a factor of $O_{corravg}(L,M,N,N_p)/O_{corrbase}(L,M,N,Q)=3*L*M*N*N_p/L*M*N*4/Q=3*N_p*Q/4=48$.

The computational requirements of the average and correlate velocity estimator described herein relative to the average and correlate computation of a base CFM system for Q=4 and $N_p$=16 is a factor of $O_{avecorr}(L,M,N,N_p,Q)/O_{corrbase}(L,M,N,Q)=3*L*M*N*(N_p+4)/Q/L*M*N*4/Q=3*(N_p+4)/4=15$.

The computational requirements of the average and correlate velocity estimator with the average and decimation performed in hardware as described herein relative to the average and correlate computation of a base CFM system for Q=4 and $N_p$=16 is a factor of $O_{avecorr}(L,M,N,N_p,Q)/O_{corrbase}(L,M,N,Q)=3*L*M*N*4/Q/L*M*N*4/Q=3$.

From the foregoing, the computational requirements of the average and correlate approach described herein are approximately 3 to 16× less than the computational requirements of the correlate and average velocity estimator of U.S. Pat. No. 6,859,659 B1 relative to the average and correlate computation of a base CFM.

The computational requirements of the autocorrelation for the combination of the 4-beams-2-lines beam-former and the average-and-correlate vector-velocity estimation as described herein relative to the average and correlate computation of a base CFM system for Q=4 and $N_p$=16 is a factor of 2*L*M*N*4/Q/L*M*N*4/Q=2. For a wideband CFM (Q=2 only for CFM), the factor is 1.

Generally, the above example shows that the computational requirements for implementing the correlate and average velocity estimator of U.S. Pat. No. 6,859,659 B1 in a base CFM system may increase by a factor of 48, which may add cost to a new ultrasound imaging system and/or prohibit VFI from being implemented on an existing ultrasound imaging system.

However, the computational requirements for implementing the combination of the 4-beams-2-lines beam-former and the average-and-correlate vector-velocity estimation as described herein in the base CFM may only increase by a factor of 2 or none at all, rendering the approach described herein well-suited to implement VFI capabilities in a base CFM systems (new and/or existing) to add VFI capabilities.

The lateral-velocity estimation can be optimized by compensating, fully or partially, for the axial-velocity component described in U.S. Pat. No. 6,859,659 B1. For this, the lag k autocorrelation estimator versus input sample $n_0$ is defined as shown in EQUATION 6:

$$\overline{R}_k(n_0) = \frac{1}{(N-k)N_p} \sum_{i=0}^{N-k} \sum_{n=-\frac{N_p}{2}}^{\frac{N_p}{2}-1} r^*\left(i, n+n_0-\frac{n_s(n_0)}{2}\right)$$

$$r\left(i+k, n+n_0-\frac{n_s(n_0)}{2}\right),$$

EQUATION 6 where $n_s(n_0)$ is the axial movement compensation sample-delay versus input sample $n_0$ given by EQUATION 7:

$$n_s(n_0) = \text{round}\left(k\frac{2V_z(n_0)}{c}T_{PRF}F_s\right),$$

EQUATION 7 where round( ) is the round-to-nearest-integer operator, $V_z(n_0)$ is the axial-velocity component for input sample $n_0$, c is the speed of sound, $T_{PRF}$=1/PRF is the pulse-repetition time, and $F_s$ is the sampling-frequency.

The two autocorrelation estimations for the lateral-velocity estimation takes the $r_1(i, n)$ and $r_2(i, n)$ as input, where $r_1(i, n)$ and $r_2(i, n)$ is the RF-sample of the received signal for shot i and sample n of two parallel receive beams. The input signals $r_1(i, n)$ and $r_2(i, n)$ are formed by the spatial-quadrature input signal $r_{sq}(\ )$ and the temporal-Hilbert transformed spatial-quadrature signal $r_{sqh}(\ )$ shown in EQUATIONS 8 and 9:

$$r_1(i,n) = r_{sq}(i,n) + jr_{sqh}(i,n), \text{ and}$$

EQUATION 8

$$r_2(i,n) = r_{sq}(i,n) - jr_{sqh}(i,n).$$

EQUATION 9

However, the axial-velocity compensation of EQUATION 6 is directly linked to the autocorrelation estimator of EQUATION 3 and the high computational requirements.

The following describes an alternate approach, based on EQUATIONS 4 and 5.

First, a more detailed description of the use of EQUATION 4 and 5 is given. For the lateral-velocity estimator, two RF-signal beams are received in parallel to form the spatial-in-phase r(i, n) and spatial-quadrature field signals $r_{sq}(i, n)$. These two signals are temporally-Hilbert transformed into the (I,Q)-signals $r_{even}(i, n)$ and $r_{odd}(i, n)$.

The input signals, as shown in FIG. 3, are band-pass filtered, temporally-Hilbert transformed and decimated by Q by the preprocessing circuitry 212 into the two intermediate (I,Q)-signals $R_{even}(i, n)$ and $R_{odd}(i, n)$ with n=m*Q, where m is the decimated sample m. The $r_{sq}(i, n)$ and $r_{sqh}(i, n)$ signals with n=m*Q are generated as shows in EQUATIONS 10 and 11:

$$r_{sq}(i,n) = \text{Re}\{r_{even}(i,n)\} + j\text{Re}\{r_{odd}(i,n)\}, \text{ and}$$

EQUATION 10:

$$r_{sqh}(i,n) = \text{Im}\{r_{even}(i,n)\} + j\text{Im}\{r_{odd}(i,n)\}.$$

EQUATION 11:

where Re{ } is the real-part operator, Im{ } is the imaginary-part operator, and n=m*Q. From these, the signals $r'_1(i, n)$ and $r'_2(i, n)$ are generated via EQUATIONS 8 and 9 for n=m*Q, which are then used as input to the intermediate sum in EQUATION 4 by substituting r(i, n) in EQUATION 4 with $r'_1(i, n)$ and $r'_2(i, n)$ respectively for the two required autocorrelation computations.

The axial-velocity compensation in EQUATION 6, performed by sample-delay of r(i, n), is equivalent to multiplying the input (I,Q)-signals $r_{even}(i, n)$ and $r_{odd}(i, n)$ with an axial-velocity compensation signal u(i, n) before forming the $r_{sq}(i, n)$ and $r_{sqn}(i, n)$, leading to an axial-velocity compensation given by EQUATIONS 12 and 13:

$$r_{sq}(i,n) = \text{Re}\{r_{even}(i,n)u(i,n)\} + j\text{Re}\{r_{odd}(i,n)u(i,n)\}, \text{ and}$$

EQUATION 12:

$$r_{sqh}(i,n) = \text{Im}\{r_{even}(i,n)u(i,n)\} + j\text{Im}\{r_{odd}(i,n)u(i,n)\}.$$

EQUATION 13:

where $$u(i, n) = \exp\left(-j2\pi\frac{2v_z(n)}{c}f_0T_{PRF}i\right),$$

$V_z(n)$ is the axial-velocity estimate versus input sample n=m*Q, c is the speed of sound, and $T_{PRF}$=1/PRF. Computation of the axial-velocity compensation signal u(i, n) can be performed by known and/or other approaches.

Figure 4:
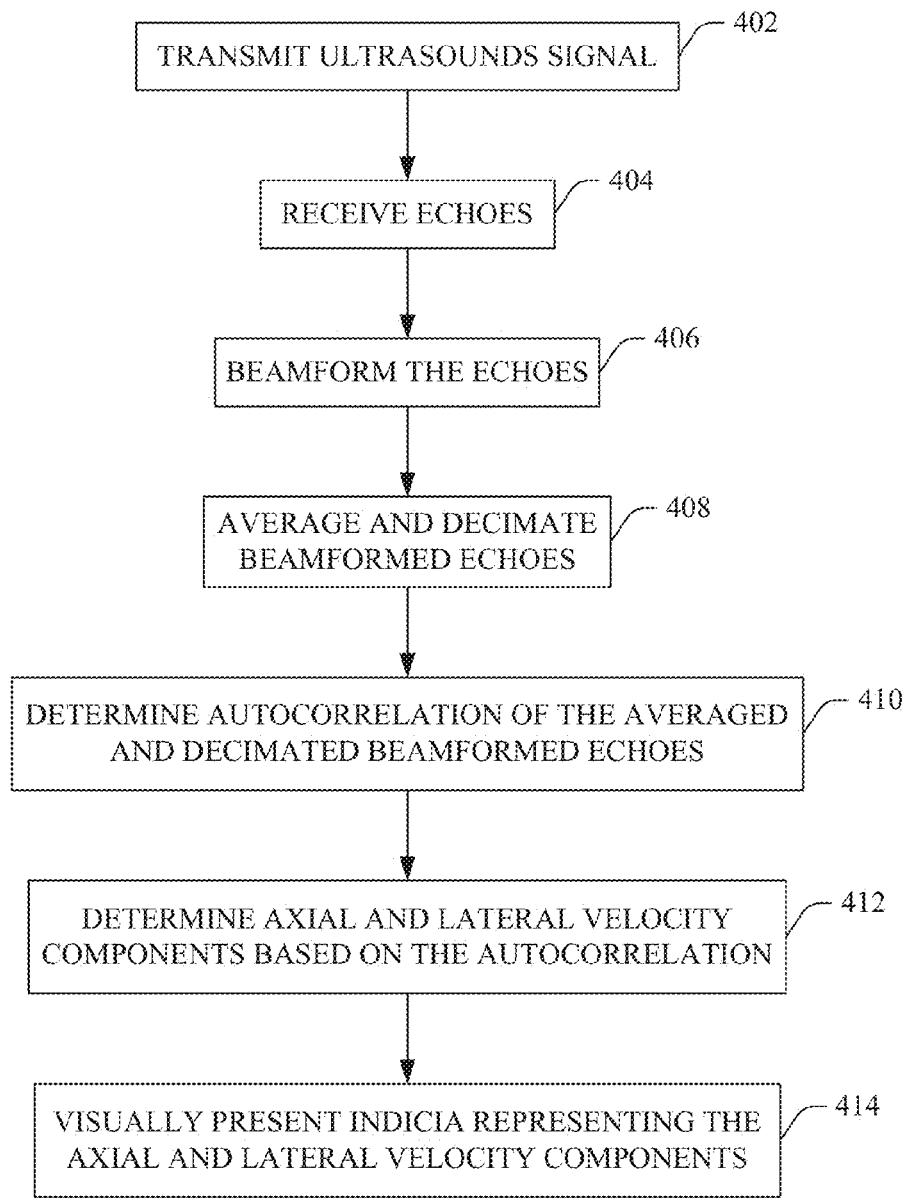
FIG. 4 illustrates an example ultrasound imaging method.

FIG. 4 illustrates an example method.

It is to be understood that the following acts are provided for explanatory purposes and are not limiting. As such, one or more of the acts may be omitted, one or more acts may be added, one or more acts may occur in a different order (including simultaneously with another act), etc.

At 402, an ultrasound signal is transmitted into a field of view.

At 404, a set of echoes, generated in response to the ultrasound signal traversing flowing structure in the field of view, are received.

At 406, the set of received echoes are beamformed, generating a set of beamformed signals, as discussed herein and/or otherwise.

At 408, the set of beamformed signals is basebanded, averaged and decimated, as discussed herein and/or otherwise.

At 410, an autocorrelation is determined for the averaged and decimated set of beamformed signals, as discussed herein and/or otherwise.

At 412, an axial velocity component signal and a lateral velocity component signal are determined based on the autocorrelation, as discussed herein and/or otherwise. The axial and lateral velocity components indicate a direction and a speed of the flowing structure in the field of view.

At 414, indicia representing the axial and lateral velocity components are displayed in connection with an ultrasound image.

The methods described herein may be implemented via one or more processors executing one or more computer readable instructions encoded or embodied on computer readable storage medium such as physical memory which causes the one or more processors to carry out the various acts and/or other functions and/or acts. Additionally or alternatively, the one or more processors can execute instructions carried by transitory medium such as a signal or carrier wave.

The application has been described with reference to various embodiments. Modifications and alterations will occur to others upon reading the application. It is intended that the invention be construed as including all such modifications and alterations, including insofar as they come within the scope of the appended claims and the equivalents thereof.

What is claimed is:

1. An ultrasound imaging system, comprising:
   a transducer array, with an array of transducer elements, that transmits an ultrasound signal and receives a set of echoes generated in response to the ultrasound signal traversing a flowing structure;
   a beamformer that beamforms the set of echoes, generating a beamformed signal;
   a pre-processor that performs basebanding, averaging and decimation of the beamformed signal and determines an autocorrelation of the basebanded, averaged and decimated beamformed signal; and
   a velocity processor that generates an axial velocity component signal and a lateral velocity component signal based on the autocorrelation,
   wherein the axial and lateral velocity components indicate a direction and a speed of the flowing structure in the field of view.

2. The system of claim 1, wherein the pre-processor decimates the beamformed signal by a factor having a value in a range of two to eight.

3. The system of claim 1, wherein the pre-processor and the velocity processor are different components.

4. The system of claim 1, wherein the velocity processor includes the pre-processor.

5. The system of claim 1, wherein the beamformer generates only one beamformed signal each scan-line for the axial velocity component.

6. The system of claim 1, wherein the beamformer generates at least two beamformed signals for at least two scan-lines for the lateral velocity component.

7. The system of claim 1, wherein the beamformer generates at least four beamformed signals for at least two scan-lines for display.

8. The system of claim 1, wherein the beamformer generates multiple beamformed signals and multiple scan-lines each acquisition.

9. The system of claim 1, wherein the beamformer operates with a sample frequency to center frequency ratio with a value in a range of two to four.

10. The system of claim 1, further comprising:
    a rendering engine and a display, wherein the rendering visually presents graphical indicia, via the display, representing the axial and lateral components in connection with an ultrasound image of the field of view.

11. A pre-processor for a velocity processor of an ultrasound console configured for velocity flow imaging, the pre-processor, comprising:
    a basebander that demodulates the input beamformed signals into an basebanded complex signal;
    an averager that averages a set of basebanded input signals;
    a decimator that decimates the averaged set of beamformed signals by a decimation factor in a range of two to eight; and
    an autocorrelator that determines an autocorrelation of the averaged and decimated set of beamformed signals,
    wherein the autocorrelation is used to generate an axial velocity component signal and a lateral velocity component signal.

12. An apparatus, comprising:
    a pre-processor that performs basebanding, averaging and decimation of a beamformed ultrasound signal and determines an autocorrelation of the basebanded, averaged and decimated beamformed signal; and
    a velocity processor that generates an axial velocity component signal and a lateral velocity component signal based on the autocorrelation, wherein the axial and lateral velocity components indicate a direction and a speed of the flowing structure in the field of view.

* * * * *